US006495850B1

(12) United States Patent
Struye et al.

(10) Patent No.: US 6,495,850 B1
(45) Date of Patent: *Dec. 17, 2002

(54) METHOD FOR READING A RADIATION IMAGE THAT HAS BEEN STORED IN A PHOTOSTIMULABLE SCREEN

(75) Inventors: Luc Struye, Mortsel (BE); Paul Leblans, Kontich (BE)

(73) Assignee: Agfa-Gevaert, Mortsel (BE)

( * ) Notice: Subject to any disclaimer, the term of this patent is extended or adjusted under 35 U.S.C. 154(b) by 47 days.

This patent is subject to a terminal disclaimer.

(21) Appl. No.: 09/595,182

(22) Filed: Jun. 16, 2000

Related U.S. Application Data

(60) Provisional application No. 60/142,276, filed on Jul. 2, 1999, and provisional application No. 60/159,004, filed on Oct. 8, 1999.

(51) Int. Cl.⁷ .......................... A61B 6/00; G01N 23/04; G03C 5/16; G11B 7/135; G21K 4/00
(52) U.S. Cl. ....................................... 250/586; 250/581
(58) Field of Search ................. 250/581, 582, 250/584, 586

(56) References Cited

U.S. PATENT DOCUMENTS

| 5,028,509 A | | 7/1991 | Shimada et al. | |
| 5,266,803 A | * | 11/1993 | Heffelfinger | 250/582 |
| 5,874,744 A | * | 2/1999 | Goodman et al. | 250/584 |
| 6,259,112 B1 | * | 7/2001 | Lim | 250/581 |

FOREIGN PATENT DOCUMENTS

| EP | 0174875 | * | 6/1990 | C09K/11/64 |
| EP | 0 174 875 | | 6/1990 | |
| JP | 3262188548 A | * | 8/1987 | H04N/1/04 |

* cited by examiner

Primary Examiner—Georgia Epps
Assistant Examiner—Alicia Harrington
(74) Attorney, Agent, or Firm—John A. Merecki; Hoffman, Warnick & D'Alessandro

(57) ABSTRACT

A method for reading a radiation image that has been stored in a photostimulable phosphor screen. The phosphor screen includes a divalent europium activated cesium halide phosphor wherein the halide is at least one of chloride and bromide. Light emitted by the phosphor screen upon stimulation is separated from stimulation light using a filter including a dye.

14 Claims, 2 Drawing Sheets

METHOD FOR READING A RADIATION IMAGE THAT HAS BEEN STORED IN A PHOTOSTIMULABLE SCREEN

This application claims the benefit of copending U.S. Appln. Ser. No. 60/142,276 filed Jul. 2, 1999 and Appln. Ser. No. 60/159,004 filed Oct. 8, 1999.

FIELD OF THE INVENTION

BACKGROUND OF THE INVENTION

Radiation image recording systems wherein a radiation image is recorded on a photostimulable phosphor screen by exposing said screen to image-wise modulated penetrating radiation are widely used nowadays.

Screens which are suitable for this application comprise e.g. a BaFX: $Eu^{2+}$phosphor or a divalent europium activated cesium halide phosphor wherein said halide is at least one of chloride and bromide.

The recorded image is reproduced by stimulating the exposed photostimulable phosphor screen by means of stimulating radiation and by detecting the light that is emitted by the phosphor screen upon stimulation and converting the detected light into an electrical signal representation of the radiation image.

In a specific embodiment light emitted by the phosphor screen upon stimulation is detected by means of an array of charge coupled devices. In order to obtain a good collection efficiency the light emitted by the phosphor screen upon stimulation is guided by means of a light guide onto the array of charge coupled devices.

In one embodiment this light guide is implemented in the form of a fibre optic plate. A fibre optic plate consist so a number of of juxtaposed optical fibres that together form a two-dimensional light guiding array. The first dimension of the array corresponds with the length of a scan line on the photostimulable phosphor screen while the second dimension covers the width of the array of transducer elements. In this way the light emitted when stimulating a scan line on the photostimulable phosphor screen is guided onto the array of transducer elements in a point-by-point like fashion.

The light which is used for stimulating the phosphor screen has to be separated from the light emitted by the screen upon stimulation.

An easy way to obtain separation of stimulating light from emission light is to use an optical filter in between the light input face of the fibre optic plate and the phosphor screen.

Coloured glass filters are widely used for this purpose.

Optimal resolution is obtained when the fibre optic plate is in close contact with the phosphor screen.

However, coloured glass filters are rather thick. The provision of a coloured glass filter in between the fibre optic plate and the phosphor screen is incompatible with the requirement of having close contact between the fibre optic plate and screen.

In case a CsBr:Eu phosphor is used, the stimulating light source is a light source emitting in the range of 600 to 800 nm. The filter should absorb the laser light to a large extent while at the same time the absorption of the light emitted upon stimulation, which has a maximum at 440 nm, should be minimal.

Optimally the optical density of the filter at the stimulation wavelength range should be at least 8 while the transmission at the emission wavelength should be higher than 75% resulting in a density equal to or less than 0.12. Reaching an optical density of 8 means that the laser light is attenuated with factor $10^7$ (Absorption=99.999999%)

To achieve these specifications by means of a glass filter such as a BG 39 Schott filter, the thickness of the filter should at least be 7 mm.

In case of a read out apparatus as described higher wherein the light emitted by the phosphor screen is guided to the array of transducer elements via a fibre optics plate, the gap between the input face of the fibre optic plate and the phosphor screen can only be approximately 100 micrometer in order to attain high resolution. It is thus clear that a glass filter is unsuitable for this application.

In case the fibre optic plate is replaced by an array of microlenses or a selfoc array this gap would attain a value in the range of 2 to 3 mm. Even in this case the use of a glass filter as described higher would be impossible.

OBJECTS OF THE INVENTION

It is an object of the present invention to provide a compact system for reading a radiation image that has been stored in a photostimulable phosphor screen wherein stimulation light and light emitted by the screen upon stimulation are optically separated.

Further objects of the invention will become apparent from the description hereafter.

SUMMARY OF THE INVENTION

The above mentioned objects are realised by a system for reading a radiation image that has been stored in a photostimulable phosphor screen comprising at least one source of stimulating radiation, an array of transducer elements arranged for detecting light emitted upon stimulation and for converting said light into a signal representation of said image, filtering means for preventing light emitted by said source of stimulation light from being detected by said transducer elements, wherein said phosphor screen comprises a divalent europium activated cesium halide phosphor wherein said halide is at least one of chloride and bromide, and said filtering means comprises a dye.

In a specific embodiment said filtering means comprise a dye that has an absorption spectrum having an absorption peak within the range of 600 to 800 nm, the maximum of said peak attaining a value corresponding with at least 99% absorption, and the absorption in the range of 400 to 500 nm being less than 25%.

In a specific embodiment the dye is dissolved in a binder such as a gelatine, a lacquer such as Mowilith CT5 (Hoechst) etc.

A filter based on a dye-gelatine composition is preferred because the filter can be made very thin so that it can be placed in between the light input face of the light guiding means and the phosphor screen. The light input face of the light guiding means is the face where the light emitted by the phosphor screen upon stimulation enters the light guiding means.

The composition of dye and binder can be self-supporting. Otherwise it can be provided on a support such as a PET support.

Alternatively it is also possible to adhere the mixture of gelatine and dye to the light entrance face of the light guiding means.

Still alternatively the composition of dye and gelatine can be coated onto the photostimulable phosphor screen itself.

In on embodiment according to the present invention a divalent europium activated cesium halide phosphor screen wherein said halide is at least one of chloride and bromide is used. Such a phosphor is known in the art and has for example been disclosed in EP-A-174 875 (and U.S. Pat. No. 5,028,509). The phosphor is especially well suited for manufacturing 'binderless' phosphor screens. Binderless phosphor screens provide optimal sharpness.

It is advantageous however to use a CsX:Eu phosphor wherein X represents a halide selected from the group consisting of Br and Cl, which is obtained by the following method:

mixing CsX with between $10^{-3}$ and 5 mol % of a Europium compound selected from the group consisting of $EuX'_2$, $EuX'_3$ and $EuOX'$, X' being a member selected from the group consisting of F, Cl, Br and I, firing the mixture at a temperature above 450° C.

cooling said mixture and recovering the CsX:Eu phosphor.

A phosphor that has been obtained as a result of the above method of preparation has an increased conversion efficiency compared to the state of the art divalent europium activated cesium halide phosphor. The phosphor can be stimulated by means of a lower amount of stimulation energy.

A photostimulable phosphor screen using such a phosphor is preferably obtained by the method of preparing said CsX:Eu phosphor by firing a mixture of said CsX with between $10^{-3}$ and 5 mol % of an Europium compound selected from the group consisting of $EuX'_2$, $EuX'_3$ and $EuOX'$, X' being a halide selected from the group consisting of F, Cl, Br and I and applying said phosphor on a substrate by a method selected from the group consisting of physical vapor deposition, thermal vapor deposition, chemical vapor deposition, radio frequency deposition and pulsed laser deposition.

This method of preparation is advantageous because it allows to deposit the phosphor in the form of needle-shaped crystals. These needle-shaped phosphor crystals act as light guides so that they reduce the lateral spreading of light in the phosphor layer. Reduced lateral light spread leads to images of higher resolution.

The needle shaped crystals will in the following be referred to as 'needles' and the phosphor layer comprising needle shaped crystals will in the following be referred to as the 'needle layer'.

Alternatively a phosphor screen containing a CsX:Eu stimulable phosphor, wherein X represents a halide selected from the group consisting of Br and Cl can also be manufactured by performing the steps of:

bringing multiple containers of said CsX and an Europium compound selected from the group consisting of $EuX'_2$, $EuX'_3$ and $EuOX'$, X' being a halide selected from the group consisting of F, Cl, Br and I in condition for vapor deposition and depositing, by a method selected from the group consisting of physical vapor deposition, thermal vapor deposition, chemical vapor deposition, electron beam deposition, radio frequency deposition and pulsed laser deposition, both said CsX and said Europium compound on a substrate in such a ratio that on said substrate a CsX phosphor, doped with between $10^{-3}$ and 5 mol % of an Europium compound, is formed.

This method of preparation is advantageous because it likewise allows to deposit the phosphor in the form of needle-shaped crystals. These needle-shaped phosphor crystals act as light guides so that they reduce the lateral spreading of light in the phosphor layer. Reduced lateral light spread leads to images of higher resolution.

This specific phosphor as well as the methods of preparation have been disclosed in U.S. provisional applications Nos. 60/159,004 and 60/142,276 which are incorporated herein by reference.

To obtain a good resolution the light used for stimulating the phosphor and the light emitted by the so-called needles of the phosphor should be guided within the needles as much as possible. When the light leaves the needle, it is partially reflected and diffused by the surface of the substrate material or of the protective layer of the screen. The addition of an absorbing layer would result in a better resolution. An absorbing layer however results in a lower sensitivity.

A layer than has different reflective properties for stimulation or emission light can be provided to solve this problem.

An embodiment of such a layer is a multilayer dielectric mirror, more specifically a so-called hot or a cold mirror. Hot and cold mirrors are for example provided by the company Melles Griot.

The filter 03 MHG 007 of Melles Griot is a hot mirror reflecting wavelengths longer than 650 nm and transmitting wavelengths within the range 400 to 650 nm.

The filter 03 MCS 005 of Melles Griot is a cold mirror reflecting short wavelengths in the range from 400 to 700 m and transmitting to a large extent these wavelengths that are longer than 700 nm.

The selection of a cold or a hot mirror depends on the design of the read out equipment.

In a flying spot scanner the light emitted upon stimulation cannot cause a loss of resolution. In this case the emitted light can be reflected, but the stimulating light should be transmitted.

In case a flying spot scanner is used for read out of the photostimulable phosphor screen it is preferred to provide a cold mirror in between the substrate layer (glass) and the phosphor needle layer. Alternatively it can be used as protective layer on top of the screen. Also combinations can be used where e.g. a cold mirror is used between the phosphor layer and the glass and a hot mirror is used on top of the screen.

On the other hand in case a read out device is used wherein pixels of a complete line are stimulated simultaneously, reflection of the stimulation light cannot result in a loss in resolution. In this case reflection of the light emitted upon stimulation is to be avoided. When this type of read out equipment is used, a hot mirror is preferably used between the substrate layer (glass) and the phosphor needle layer. Alternatively it can also be used as a protective layer on top of the phosphor needle layer.

The specific phosphors that are described higher can be stimulated by means of light in the wavelength range from 500 to 1100 nm, optimally in the range of 600 to 800 nm. The stimulation spectrum has a peak at 685 nm. The light emitted by the phosphor screen upon stimulation is situated in the range of 350 to 750 nm, the emission spectrum having a maximum at 440 nm.

In accordance with the present invention a dye is used that has a high absorption at the stimulation wavelength range and a very low absorption at the wavelength of the light emitted upon stimulation.

A separation factor is defined as the ratio of the absorption amount at the stimulation wavelength and the absorption at the emission wavelength.

In case of the above phosphors this ratio is given by the absorption at 685 nm divided by the absorption at 440 nm.

The density of a filter is proportional to its separation factor. The density at the laser wavelength is preferably higher or equal to 8, corresponding with a transmission lower than $10^{-6}$%, while the density at the emitted wavelength is preferably less than 0.12 (corresponding to a transmission of 75%). The separation factor is preferably higher than 8/0.12=67.

The following dyes have the required characteristics:

Formula 1: Cryptocyanine
(1,1'-Diethyl-4,4'-carbocyanine Iodide)

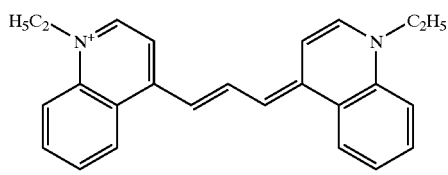

Formula 2: Oxatricarbocyanine
(3,3,-Dimethyloxatricarbocyan Iodide)

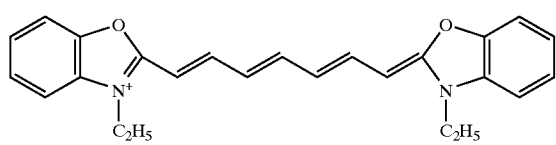

Formula 3: Indotricarbocyanine
(1,1'-Diethyl-2,2'-dicarbocyanine Iodide)

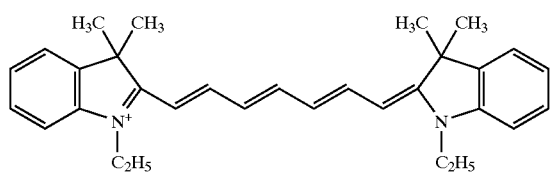

Formulae 4: Thiadicarbocyanine
(3-Diethylthiadicarbocyanine Iodide)

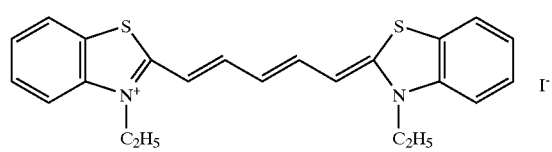

Formula 5: Thiatricarbocyanine
(3,3'-Diethylthiatricarbocyanine Iodide)

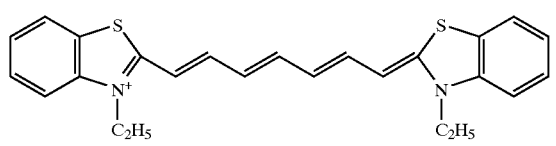

Formula 6: Rhodamine 800
(8-Cyano-2,3,5,6,11,12,14,15-octahydro-1H,4H,10H,13H-diquinolizino [9;9a,1-bc:9', 9a',1-h]xanthylium Perochlorate

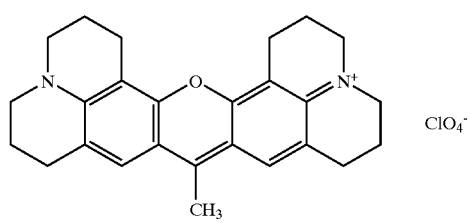

Formule 7: Magnesium Phthalocyanine (MgPc)

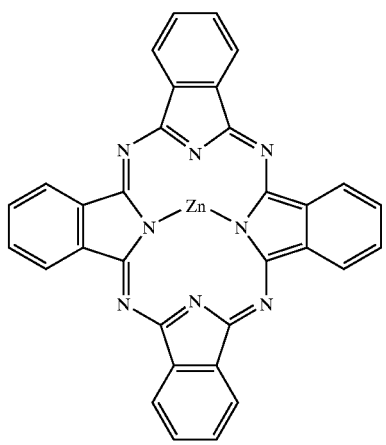

Formule 8: Zinc Phthalocyanine (ZnPc)

Formula 9: Methylene Blue

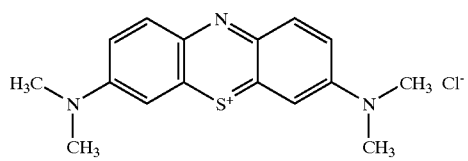

Formula 10: Indocyanine Green

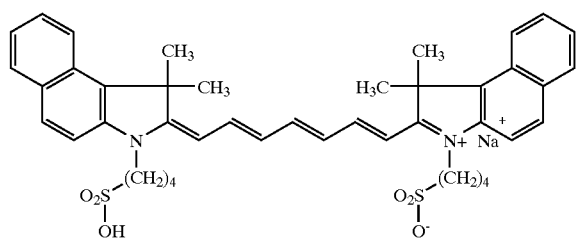

Formula 11
Copper(II) 3,10,17,24-tetra-tert-butyl-1,8,15,22-tetrakis (dimethylamino)-29H,31H-phthalocyanine Formula 12
Vanadyl 3,10,17,24-tetra-tert-butyl-1,8,15,22-tetrakis (dimethylamino)-29H,31H-phthalocyanine Formula 13
Vanadyl 5,14,23,32-tetraphenyl-2,3-naphthalocyanine
Formula 14 : Sulfonated Cu-phthalocyanine

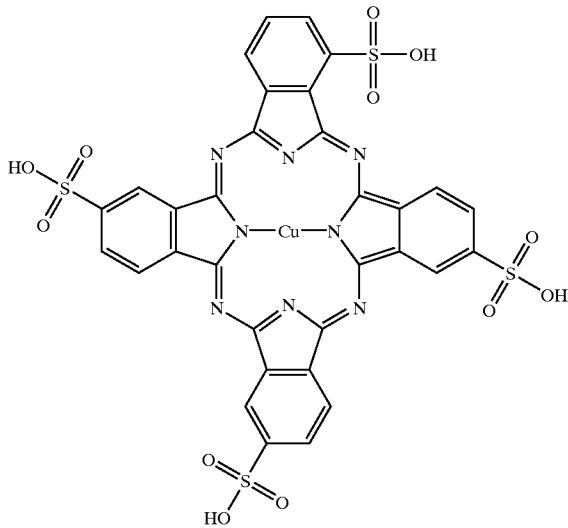

Formula 15 Carbazine

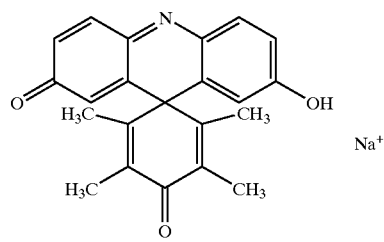

In general cyanine dyes are preferred.

Among these the dye Cryptocyanine has a separation factor of 721, the dye oxatricarbocyanine (C7) dye has a separation factor of 120 and the dye Indotricarbocyanine (C7) dye has a separation factor of 60.4 at the above wavelengths and are thus very well suited.

The dyes Methylene Blue and Rhodamine 800 can also be used.

All dyes show fluorescence at longer wavelengths than the absorbed laser wavelength. The emission spectrum of Cryptocyanine has a maximum at 723 nm. The emission spectrum of oxatricarbocyanine has a maximum at 713 nm.

In order to absorb this fluorescent light a second filter can be used. This additional filter can be a glass filter since a relatively thin filter is adequate. For example a coloured BG39 Schott glass filter (Schott being a trade name) of a thickness of 2 mm is well suited.

Good results are obtained with a combination of a gelatine filter made with Methylene Blue (400 $\mu$gram/m) and a filter BG39 of 2 mm thick. The filters are placed so that the laser light passes first the Methylene Blue and secondly the filter BG39.

A density of 8 can be reached with this combination resulting in a transmission of 52%.

The fluorescence light can also be attenuated using a optical coating made with dielectrical layers (TiO$_2$). The filter types Blue Cyan and DT Blue from the company Balzers are well suited.

A combination of a dye with both a colored glass filter and a coating of dielectrical layers is possible.

To absorb the fluorescence light also other dyes than the above mentioned can be used. Here the dyes indotricarbocyanine and thiadicarbocyanine and thiatricarbocyanine can be used. Using a filter where no glass or dielectric layers but only dyes are used to absorb the light results in a very thin layer than can be placed between the phosphor plate and a fiber optic plate.

It is also possible to add this additional dye layer to the fiber optic plate or to the phosphor screen. In this way the optical filter can be integrated in the image screen itself.

It is known that the optical characteristics of a dye can change by exposing them to light. In order to minimize the degradation of the dyes, some additives can be added.

Alternatively a combination can be made of a first dye filter with a second filter such as a BG39 Schott filter of 1 mm thickness.

The dye filter can also be placed between two coloured glass filters of 1 mm. The laser light can be attenuated with factor 30 with the 1 mm filter BG39 that is placed between the light source and the dye filter. A second 1 mm thick filter BG39 that is placed between the dye filter and the detector is appropriate to attenuate the fluorescence of the dye.

Another aspect of the present invention relates to the fact that a fibre optic plate can be used for directing light emitted by the phosphor screen onto the array of transducer elements. A fibre optic plate consist so a number of juxtaposed optical fibres that together form a two-dimensional light guiding array. A fibre optic plate is an advantageous light guiding means because it can be made very compact and has high resolution and high collection efficiency.

In order to obtain separation of stimulation light and light emitted by the phosphor upon stimulation and to prevent that stimulation light is detected by the array of transducer elements the fibres of the fibre optic plate can be composed by means of coloured fibres (e.g. made of glass or plastic).

The optical characteristics that are required are (1) a high absorption of the stimulating wavelength range and (2) at the same time a high transmission of the emission wavelength.

Because of the structure of the phosphor screen obtained by applying the methods described higher, a higher sharpness and higher sensitivity is obtained. Not only the image screen should offer high sharpness, also the read out equipment should not degrade the sharpness.

The lasers that are used mostly in read out equipment for digital radiography are diode lasers. These lasers generate nearly monochromatic light. Nevertheless they also produce weak light at other wavelengths than the laser line itself. This is called the LED-light of the laser. The laser is also functioning as an LED and is producing light in the spectrum of an LED. Some wavelengths of this LED-light are shorter than the laser-line, others are longer.

These different wavelengths are transmitted differently by the optical filter.

In the case the above described csBr:Eu phosphor types are used, a filter BG39 of Schott attenuates the laser-line of a diode laser-emitting at 685 nm very well while it transmits light at 440–460 nm. Although the filter has a steep characteristic, light at shorter wavelengths than the laser wavelength (e.g. 650 nm) is not absorbed strongly.

The shorter wavelengths of the LED-light pass the BG39-filter partially and are detected as a residual signal. When the BG39 filter should attenuate the LED-light to a sufficient extent, it should be as thick as 7 mm.

If the LED-light could be eliminated the thickness of the filter could be decreased to 4 mm. It is obvious that the transmission for the emitted light is higher for the filter with thickness 4 mm.

Furthermore, the LED-light does not follow the same direction as the laser light and hence might not be focused onto the same position on the phosphor screen as the laser light. The LED light reaches the phosphor screen in the form of a halo around the small laser spot. Since the LED light stimulates the phosphor screen in addition to the stimulation by the laser light, the resolution is decreased.

The above problems can be solved and an improvement in sensitivity and sharpness can be obtained by adding an optical filter or a set of optical filters in between the stimulating laser and the photostimulable phosphor screen in order to attenuate the LED-light of the laser.

In one embodiment wherein a diode laser emitting at 685 nanometer is used as stimulating light source, a RG 665 Schott filter having a thickness of 2 mm was placed in between the laser and the screen. In this way wavelengths shorter than 665 nm were attenuated while longer wavelengths are transmitted. The laser line at 685 mm was only attenuated by 5%.

Further advantages and embodiments of the present invention will become apparent from the following description and drawings.

DETAILED DESCRIPTION OF THE INVENTION

Figure 1:
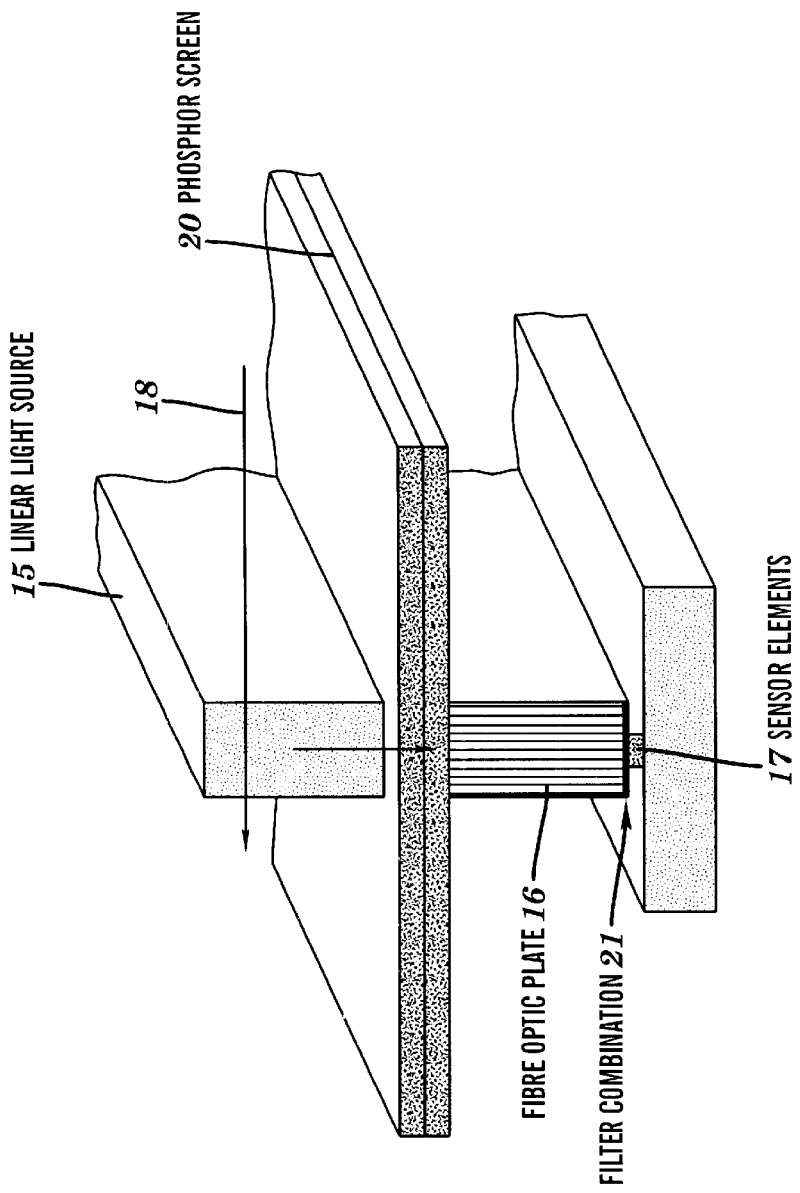
FIG. 1 shows an embodiment of photostimulable phosphor read out unit according to the present invention, referred to as scan-head type.

An embodiment of a read out unit, referred to as scan-head type read out unit type is shown in FIG. 1.

In one embodiment the read out unit comprises a linear light source (15) for emitting stimulating light onto the photostimulable phosphor screen.

This linear light source comprises 4096 individual laser diodes arranged in a row. This light source provides simultaneous illumination of all pixels of a single line of the photostimulable phosphor screen.

The phosphor screen (20) comprises a divalent europium activated cesium halide phosphor which is obtained by performing the following steps:

mixing CsX with between 10-3 and 5 mol % of a Europium compound selected from the group consisting of EuX'2, EuX'3 and EuOX', X' being a member selected from the group consisting of F, Cl, Br and I, firing the mixture at a temperature above 450° C.

cooling the mixture and recovering the CsX:Eu phosphor.

The read out unit further comprises a fiber optic plate (16) for directing light emitted by the phosphor screen upon stimulation onto a linear array of sensor elements (17), more particularly charge coupled devices. The fiber optic plate (16) comprises a number of parallel mounted light guiding fibers arranged so as to guide the light emitted by each individual element of an illuminated line onto a sensor element.

In between the output of fiber optic plate and the array of sensor elements a filter combination (21) is placed.

The filter combination is a sandwich of two filters BG39 glass filters of 1 mm thickness. In between the two BG 39 glass filters a dye filter is placed. The dye filter comprises a cryptocyanine dissolved in a Mowilith CT5 lacquer. The composition is coated on a transparent PET layer.

As an optimalisation a dielectric layer (such as Blue Cyan) is added to the filter BG39-1 mm that is placed between the dye layer and the array of sensor elements.

As dye the cryptocyanine is preferred because it has the highest separation factor.

However, oxatricarbocyanine and sulphonated Cu-phthalocyanine also have optimal separation characteristics.

If a glass filter is not used dicarbocyanine is preferably used to absorb the fluorescence of the cryptocyanine.

Alternatively the fiber optic plate can be replaced by an arrangement of selfoc lenses or microlenses.

Alternatives may also be envisaged for the linear light source. This linear light source can be replaced by a 'flying spot' light source. The light emitted by this light source is then deflected by a rotatable polygon mirror onto a scan line on the phosphor screen. In this way one point of this line at the time is illuminated.

In the embodiment shown in FIG. 1 the linear light source is arranged on one side of the phosphor screen, the fiber optic plate and the linear array of sensor elements being arranged on the opposite side. Either of these elements extends in the direction of a scan line.

During read out, the phosphor screen on the one hand and the assembly of fiber optic plate and sensor array on the other hand are displaced relative to each other in the direction of arrow (18).

In still another embodiment which is not shown the array of stimulating light sources, the fiber optic plate and the sensor array are arranged at the same side of the photostimulable phosphor screen.

After read out the photostimulable phosphor screen is erased so that the energy remaining in the screen after read out is released and so that the screen is in a condition for re-use.

Figure 2:
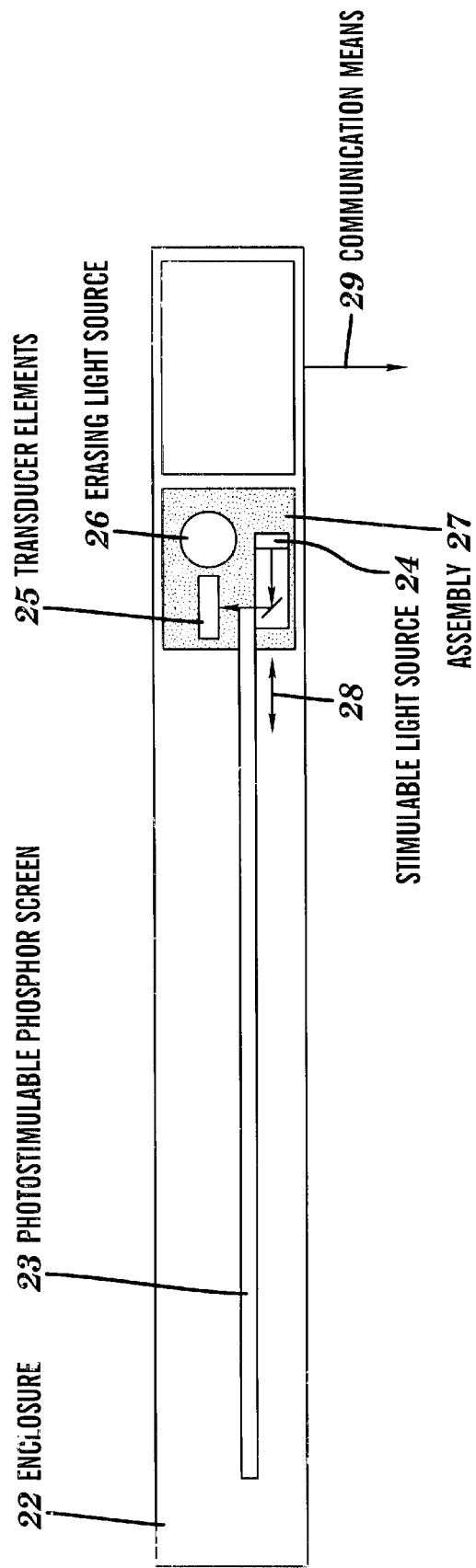
FIG. 2 shows a radiation detector according to the present invention.

Another aspect of the present invention relates to a re-usable radiation detector. This type of detector is shown in FIG. 2.

The detector comprises an enclosure (22).

Within the enclosure a photostimulable phosphor screen (23) is positioned. This screen comprises a divalent cesium halide phosphor, wherein said halide is at least one of chloride and bromide as described with reference to the first embodiment illustrated by FIG. 1.

The enclosure further comprises a source of stimulating light (24) arranged for stimulating said phosphor screen and an array of transducer elements (25) for capturing light emitted by the phosphor upon stimulation and for converting said light into an electrical signal representation. In the illustrated embodiment the source of stimulating light is a linear light source and the array of transducer elements is also a linear array. This embodiment can be made very compact and provides fast read out.

The enclosure further comprises a linear erasing light source (26) arranged substantially parallel to the stimulating light source.

The enclosure still further comprises means (not shown) for transporting the assembly (27) of stimulating light source, erasing light source and array of transducer elements relative to the phosphor screen in a so-called sub-scan direction, indicated by arrow.(28).

Means (29) are further provided for communicating the electrical signal representation output by the array of transducer elements to an external signal processing device.

In this re-usable radiation detector the phosphor screen remains inside the enclosure during irradiation, read out and erasure.

In this embodiment the stimulating light source and the array of transducer elements are arranged on opposite sides of the phosphor screen.

In an alternative embodiment these items may be arranged on the same side of the phosphor screen.

Separation of stimulation and emission light is performed by means of a filter combination as described with reference to the first embodiment shown in FIG. 1.

What is claimed is:

1. A method for reading a radiation image that has been stored in a photostimulable phosphor screen comprising:

stimulating a photostimulable phosphor screen using at least one source of stimulating radiation;

detecting light emitted by the phosphor screen upon stimulation, and converting the light into a signal representation of the image, using an array of transducer elements;

preventing light emitted by the at least one source of stimulating radiation from being detected by the array of transducer elements;

wherein photostimulable phosphor screen comprises a divalent europium activated cesium halide phosphor wherein the halide is at least one of chloride and bromide, and wherein the phosphor is obtained by:

mixing CsX, wherein X represents a halide selected from the group consisting of Cl and Br, with between $10^{-3}$ and 5 mol % of a Europium compound selected from the group consisting of $EuX'_2$, $EuX'_3$ and EuOX', X' being a member selected from the group consisting of F, Cl, Br and I;

firing the mixture at a temperature above 450° C.;

cooling the mixture; and recovering the CsX:Eu phosphor.

2. A method according to claim 1 wherein said phosphor screen is obtained by the steps of:

preparing said CsX:Eu phosphor by firing a mixture of said CsX with between $10^{-3}$ and 5 mol % of an Europium compound selected from the group consisting of $EuX'_2$, $EuX'_3$ and EuOX', X' being a halide selected from the group consisting of F, Cl, Br and I; and applying said phosphor on a substrate by a method selected from the group consisting of physical vapour deposition, thermal vapour deposition, chemical vapour deposition, radio frequency deposition and pulsed laser deposition.

3. A method according to claim 1 wherein said phosphor screen is obtained by the steps of:

bringing multiple containers of said CsX and an Europium compound selected from the group consisting of $EuX'_2$, $EuX'_3$ and EuOX', X' being a halide selected from the group consisting of F, Cl, Br and I in condition for vapour deposition; and depositing, by a method selected from the group consisting of physical vapour deposition, thermal vapour deposition, chemical vapour deposition, electron beam deposition, radio frequency deposition and pulsed laser deposition, both said CsX and said Europium compound on a substrate in such a ratio that on said substrate a CsX phosphor, doped with between $10^{-3}$ and 5 mol % of an europium compound, is formed.

4. A method according to claim 1, wherein a filtering means is used to prevent light emitted by the at least one source of stimulating radiation from being detected by the array of transducer elements.

5. A method according to claim 4, wherein the filtering means comprises a dye.

6. A method according to claim 4, wherein the filtering means is adhered to an output face of a light guiding means for guiding light emitted upon stimulation to the array of transducer elements.

7. A method according to claim 5, wherein the filtering means is coated onto the photostimulable screen.

8. A method according to claim 5, wherein the dye has an absorption spectrum having an absorption peak within the range of 600 to 800 nm, the maximum of the peak attaining a value corresponding with at least 99% absorption, and the absorption in the range of 400 to 500 nm being less than 25%.

9. A method according to claim 8, wherein the filtering means is coated onto the photostimulable phosphor screen.

10. A method according to claim 5, wherein the dye is dissolved in a binder comprising gelatine.

11. A method according to claim 5, wherein the dye is a cyanine dye.

12. A method according to claim 5, wherein the dye is cryptocyanine.

13. A method according to claim 5, wherein the dye is oxatricarbocyanine.

14. A method according to claim 5, wherein the dye is sulphonated Cu-phthalocyanine.

* * * * *

UNITED STATES PATENT AND TRADEMARK OFFICE
Certificate

Patent No. 6,495,850 B1                                            Patented: December 17, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Luc Struye, Mortsel, Belgium; Paul Leblans, Kontich, Belgium; Martin Devenney, Mountain View, CA; and Casper Reaves, San Jose, CA.

Signed and Sealed this Sixth Day of July 2004.

GEORGIA Y. EPPS
*Supervisory Patent Examiner*
Art Unit 2873